United States Patent [19]

McDonald et al.

[11] 4,254,218

[45] Mar. 3, 1981

[54] DETECTING NEISSERIA VIA IMMOBILIZED ANTIBODY-ENZYME COMPLEX

[75] Inventors: Hugh C. McDonald; Gerald Odstrchel, both of Horseheads; Milton M. Takeguchi, Big Flats, all of N.Y.

[73] Assignee: Corning Glass Works, Corning, N.Y.

[21] Appl. No.: 14,294

[22] Filed: Feb. 23, 1979

[51] Int. Cl.³ .................... C12Q 1/66; C12N 11/14
[52] U.S. Cl. .................................. 435/7; 435/176; 435/810
[58] Field of Search ............ 435/4, 7, 26, 810, 176; 23/230 B; 424/12

[56]  References Cited

U.S. PATENT DOCUMENTS

| 4,016,043 | 4/1977 | Schuurs et al. | 435/7 |
| 4,029,756 | 6/1977 | Gaafar | 435/7 |
| 4,071,409 | 1/1978 | Messing et al. | 435/176 |
| 4,140,581 | 2/1979 | Weetal | 435/7 |
| 4,166,765 | 9/1979 | Weetall | 435/26 |

Primary Examiner—Thomas G. Wiseman
Attorney, Agent, or Firm—William E. Maycock; Clinton S. Janes, Jr.

[57] ABSTRACT

A method for detecting the presence of Neisseria bacteria in a fluid sample which comprises bringing immobilized antibody specific for the enzyme 1,2-propanediol dehydrogenase which is released from such bacteria upon lysis thereof, into contact with a lysed sample, isolating the immobilized antibody or resulting immobilized antibody-enzyme complex or mixture thereof, and then testing the isolated material for enzymatic activity.

18 Claims, No Drawings

DETECTING NEISSERIA VIA IMMOBILIZED ANTIBODY-ENZYME COMPLEX

CROSS-REFERENCES TO RELATED APPLICATIONS

Patent application Ser. No. 837,366, Detecting Neisseria Bacteria, filed Sept. 28, 1877 by H. H. Weetall, now U.S. Pat. No. 4,166,765; patent application Ser. No. 837,365, Comparative Test for Neisseria, filed Sept. 28, 1977 by H. H. Weetall, now U.S. Pat. No. 4,111,752; patent application Ser. No. 837,364, Detection of Neisseria Bacteria by Immunoassay, filed Sept. 28, 1977 by H. H. Weetall; patent application Ser. No. 837,363, Immunoassay of Neisseria Bacteria by $(NH_4)_2SO_4$ Precipitation, filed Sept. 28, 1977 by H. H. Weetall, now U.S. Pat. No. 4,140,581; patent application Ser. No. 836,360, Detection and Quantitation of Neisseria via Radioimmunoassay of an Enzyme Present in Neisseria Bacteria, filed Sept. 28, 1977 by H. C. McDonald; patent application Ser. No. 837,362, Immunological Detection of Neisseria Bacteria via Labelled Antibodies, filed Sept. 28, 1977 by H. H. Weetall, now U.S. Pat. No. 4,188,381; and patent application Ser. No. 837,361, Transport System for Clinical Specimens, filed Sept. 28, 1977 by M. M. Takeguchi and H. H. Weetall, now U.S. Pat. No. 4,150,950. Each of these applications is assigned to the assignee of the present invention.

BACKGROUND OF THE INVENTION

This disclosure relates generally to tests for determining the presence of certain microorganisms and specifically to a test for detecting Neisseria bacteria via an immobilized antibody-enzyme complex, which enzyme is clinically unique to Neisseria bacteria.

The importance of quickly and accurately detecting the presence of Neisseria bacteria, especially *Neisseria gonorrhoeae,* is well recognized. Present tests for determining the presence of such organisms as *N. gonorrhoeae* include the preparation of bacterial cultures or the use of serological methods. Such tests, however, have known limitations. See, e.g., the publication, "International Symposium On Gonorrhea," edited by B. B. Diena, which is a collection of papers presented at the October, 1973 International Symposium on Gonorrhea sponsored by the Health Protection Branch, Health and Welfare, Ottawa, Canada, especially at p. 34, et seq.

A relatively simple and quick test for the presence of Neisseria in liquid samples is disclosed in related application Ser. No. 837,366, cited above. Such test is based upon the discovery of an enzyme in Neisseria bacteria which, at the time, appeared to be specific thereto. The structure of the enzyme is not fully understood and no identification thereof in the literature is known. However, the enzyme has the capability of oxidizing 1,2-propanediol and reducing nicotinamide-adenine-dinucleotide (NAD). Because of these two characteristics, the enzyme was named 1,2-propanediol dehydrogenase, which name will be used throughout this specification.

That a biochemical reaction can take place between an antigen and its homologous antibody, giving rise to an antibody-antigen complex, is well recognized. It also is well known that enzymes typically are antigenic and that, as a consequence, antibody-enzyme complexes are readily prepared. See, e.g., M. R. J. Salton, Editor, "Immunochemistry of Enzymes and Their Antibodies," John Wiley & Sons, New York, 1977; B. Cinader, Editor, "Antibodies to Biologically Active Molecules," Vol. 1 of the Proceedings of the 2nd Meeting of the Federation of European Biochemical Societies, Vienna, 21-24 April 1965, Symposium Publications Division, Pergamon Press, Oxford, 1967; B. Cinader, Consulting Editor, "Antibody to Enzymes—A Three-Component System," *Ann. N.Y. Acad. Sci.,* 103 (Art. 2), 493-1154 (1963); and C. A. Williams and M. W. Chase, Editors, "Methods In Immunology and Immunochemistry," Vol. IV, Academic Press, New York, 1977, pp. 312-375. In the case of an enzyme, however, formation of the antibody-enzyme complex frequently results in the inhibition of enzymatic activity. Such inactivation, though, can be employed as the basis of an assay for a particular enzyme. That is, the presence of the enzyme in a sample can be detected by adding to the sample antibody specific for the enzyme and monitoring the resulting mixture for a decrease in enzymatic activity.

Inhibition of the enzymatic activity of 1,2-propanediol dehydrogenase, the above-described enzyme which is clinically unique to Neisseria bacteria, is known to occur in the presence of antibodies specific for the enzyme. Indeed, this inhibition is an important factor in three of the related applications cited hereinbefore.

Application Ser. No. 837,364 discloses a method of using antibodies directed against an enzyme present in Neisseria, i.e., 1,2-propanediol dehydrogenase, to inhibit enzyme activity in a sample, thereby inferring antibody specificity on the assay for Neisseria bacteria which is in fact a test for the presence of such enzyme. The percent inhibition of the enzyme is shown to be directly proportional to the incubation time and the amount of antibody present per unit of enzyme activity. For example, at a globulin:enzyme ratio of 1.47 (mg. total globulin in the antibody preparation per International Unit of enzyme), the percent inhibition of enzymatic activity after 0.5, 1.0, and 2.0 hours is 15, 23, and 38, respectively. In other examples, the percent inhibition at globulin:enzyme ratios of 0.75 and 0.075 varied from 76 to 91 and from 23.5 to 29, respectively, with the incubation times ranging from 24 to 141 minutes and from 30 to 144 minutes, respectively.

Application Ser. No. 837,363 discloses a modification of the method described in the above application, Ser. No. 837,364, wherein ammonium sulfate precipitation of the antibody-enzyme complex serves to concentrate the complex, thereby removing interfering materials and improving the speed and precision of the method. In a preferred embodiment, the inhibitory effect of the antiserum is explicitly exhibited through a comparative test wherein one sample is contacted with antiserum and a second sample serves as a control. Clearly, the modification requires inhibition of enzymatic activity in the presence of antibody (antiserum) specific for the enzyme.

Finally, application Ser. No. 837,362 discloses two closely-related assay methods for detecting the presence of Neisseria bacteria in a sample. Both methods utilize radiolabelled antibody specific for the enzyme 1,2-propanediol dehydrogenase which is released upon lysis of the Neisseria bacteria. While neither enzymatic activity nor the inhibition thereof are required for the assay, the specification describes the use of such inhibition of enzymatic activity to titer the antiserum. Thus, undiluted antiserum resulted in a 96% inhibition of enzymatic activity. Even with dilutions of up to 1:16, the inhibition of enzymatic activity was 70% or higher.

SUMMARY OF THE INVENTION

It now has been discovered, quite unexpectedly, that immobilized antibody specific for 1,2-propanediol dehydrogenase, an enzyme found in Neisseria bacteria, will bind with the enzyme to form an immobilized antibody-enzyme complex in which the enzyme retains substantial enzymatic activity.

Accordingly, the present invention provides a method for detecting the presence of Neisseria bacteria in a fluid sample which comprises bringing immobilized antibody specific for the enzyme 1,2-propanediol dehydrogenase which is released from such bacteria upon lysis thereof, into contact with a lysed sample, isolating the immobilized antibody or resulting immobillized antibody-enzyme complex or mixture thereof, and then testing the isolated material for enzymatic activity.

The present invention also provides a method for detecting the presence of Neisseria bacteria in a fluid sample which comprises the steps of:

A. preparing a lysate of such sample;

B. combining the lysate with an immobilized antibody specific for the enzyme 1,2-propanediol dehydrogenase;

C. incubating the mixture resulting from step B;

D. separating from the incubated mixture of step C the immobilized antibody or resulting immobilized antibody-enzyme complex or mixture thereof; and E. assaying the material obtained from step D for 1,2-propanediol dehydrogenase activity.

As already indicated, the method of the present invention is useful for the clinical determination of the presence of Neisseria bacteria in a fluid sample, and especially for determining quickly and accurately whether or not an individual is infected with *Neisseria gonorrhoeae*.

DETAILED DESCRIPTION OF THE INVENTION

At the time the above-described related applications were filed, it was believed that the enzyme 1,2-propanediol dehydrogenase was unique to Neisseria bacteria. Work subsequently carried out by employees of the assignee of the present invention has shown, however, that an immunochemically similar enzyme is present in *Acinetobacter calcoaceticus*, var. *antitratus* and *lwoffi*, although in much lower concentrations.

As already indicated, interest in identifying Neisseria bacteria primarily is focused on *N. gonorrhoeae*, the organism responsible for gonorrhea, a bacterial infection of the mucous membrane of the urogenital tract. Thus, bacterial samples of greatest clinical significance typically are collected from or near the cervix uteri, e.g., from the endocervix, of females and the urethral canal of males. Because the above two Acinetobacter species are not known to be present in such two areas of the body, the presence of 1,2-propanediol dehydrogenase in such species is believed to be immaterial to the method of the present invention. Accordingly, the term "clinically unique" is employed throughout this specification to indicate that the established presence of 1,2-propanediol dehydrogenase in Neisseria bacteria is clinically significant as disclosed herein and in the related applications.

The first step in the method of the present invention comprises preparing a lysate of the sample. Such preparation can be accomplished by known means, typically by using known lysing agents or conditions. Since the purpose of the lysing step is to disrupt bacterial membranes and cell walls, thereby causing the release into the fluid medium of intracellular contents, including the enzyme 1,2-propanediol dehydrogenase (if present), any known means for accomplishing this result can be employed as long as the 1,2-propanediol dehydrogenase is not inhibited, denatured, or otherwise deleteriously affected. A suitable lysate often can be prepared by simply suspending the microbial cells present in a sample or specimen in a suitable buffer at an appropriate pH. Alternatively, the buffer suspension of cells can contain the enzyme lysozyme. In some cases, depending upon the sample source and other factors, it may be desirable to add a small amount of a chelating agent, such as ethylenediamine tetraacetic acid (EDTA), to complex with any divalent metal ions in the lysate which might interfer with the subsequent assay for enzymatic activity.

As a practical matter, Neisseria bacteria are lysed essentially completely by suspending the cells in 0.03 M Tris buffer, pH 9.0, for one hour. Under such conditions, cell lyses is about 99% complete, based on phase microscopy observations. Alternatively, the suspension period can be reduced to 0.5 hour by using 0.1 M Tris buffer. Neither a chelating agent nor lysozyme are necessary to achieve lysis.

In general, the sample can be from any source. If not already in a fluid state, the sample is added to a suitable buffer or other solution. Thus, the term "fluid sample" refers either to original, fluid samples or to samples converted to a fluid form subsequent to sample collection. Most often, the sample will be derived from a human body fluid or an exudate such as is collected on a swab or like implement.

In the second step of the present invention, the lysate is combined with an immobilized antibody specific for the enzyme 1,2-propanediol dehydrogenase. In general, antibody specific for the enzyme 1,2-propanediol dehydrogenase is generated in accordance with known procedures. Typically, however, the antiserum thus obtained is not further processed to give purified antibody. As a matter of convenience, the immobilized antibody is prepared directly from the antiserum. Thus, the immobilized antibody inevitably has associated with it immobilized proteins, e.g., globulins, of various types, none of which are significant in terms of the method of the present invention. Thus, the term "immobilized antibody" does not require any particular degree of purity, although it will be apparent to those skilled in the art that immobilized antibody preparations derived directly from antiserum will require more of such preparation per unit of enzyme activity than such a preparation derived from purified antiserum.

The immobilization of antibody in turn is carried out in accordance with well known procedures. In general, neither the carrier nor the immobilization procedure is critical, provided that significant deleterious effects are avoided. Thus, the carriers can be organic or inorganic, porous or nonporous, and in any desired shape or form. The carrier can be particulate in nature, varying from a finely-divided powder to a coarse granular material, or the carrier can be a continuous, shaped article such as a flat or curved sheet or pellet, or a three-dimensional article such as a rectangular or cylindrical tube or a complex monolith. As a practical matter, the carrier most often will be particulate and relatively finely divided, e.g., from about 20 to about 10 mesh, U.S. Standard Sieve.

Examples of suitable organic carriers include, among others, polyesters, such as poly(ethylene terephthalate); polyamides, such as nylon 6 and nylon 6.6; polyacrylates; polymethacrylates; agarose gels; dextran gels; polyolefins, such as polyethylene, polypropylene, polybutene, and polybutadiene; polystyrene; poly(vinyl chloride); poly(vinylidine chloride); and the like.

The inorganic carriers can be classified as siliceous or nonsiliceous metal oxides. Examples of siliceous carriers include glass, silica, wollastonite, bentonite, cordierite, and the like. Examples of nonsiliceous metal oxides include, among others, alumina, spinel, apatite, nickel oxide, titania, zirconia, and the like. The preferred carriers are inorganic in nature, with siliceous materials being more preferred. The most preferred carriers are silica and glass. Preferably, the carrier will be porous in order to provide a greater amount of antibody per unit volume or mass of carrier.

In general, the antibody can be immobilized by any known means which can vary from simple adsorption to chemical coupling. Adsorption, of course, usually involves contacting an aqueous solution of the antibody (antiserum) to be immobilized with the carrier for a time sufficient to permit the desired (or maximum) degree of immobilization. Chemical coupling typically involves treating the carrier with one or more chemical compounds, followed by contacting the treated carrier with an aqueous solution of the antibody. Among the chemical compounds which can be used to treat the carrier, and especially the inorganic carrier, are o-dianisidine (U.S. Pat. No. 3,983,000), polymeric isocyanates (U.S. Pat. No. 4,071,409), silanes (U.S. Pat. Nos. 3,519,538 and 3,652,761), and the like. See also U.S. Pat. Nos. 3,930,951 and 3,933,589.

The third step of the present invention comprises incubating the mixture resulting from the second step. Such incubation typically is carried out at a temperature of from about 4° C. to about 40° C. An especially suitable temperature is 37° C. Incubation times are not critical, and generally will vary from about 0.5 to about 3 hours. As a practical matter, however, incubation times in excess of one hour seldom are required.

According to the fourth step of the method of the present invention, the immobilized antibody or resulting immobilized antibody-enzyme complex or mixture thereof is separated from the incubated mixture of the third step. Such separation can be by any known means, such as centrifugation and filtration, although centrifugation is particularly effective and is preferred.

The fifth step comprises assaying the material obtained from the fourth step for 1,2-propanediol dehydrogenase activity. Such assay can be accomplished by any known means, and can be either qualitative or quantitative.

Because the enzyme oxidizes 1,2-propanediol and reduces NAD, an especially suitable procedure which is preferred comprises incubating the material obtained from the fourth step with buffer containing 1,2-propanediol and NAD and subsequently testing for the presence of reduced NAD (NADH). For example, the sample can be irradiated with ultraviolet light for a qualitative determination of the presence of the enzyme since NADH fluoresces under such radiation. Alternatively, the presence of enzyme can be quantitated by measuring, either spectrophotometrically at 340 nm or fluorometrically, the amount of NADH generated.

The present invention is further illustrated, but not limited, by the example which follows. Unless otherwise indicated, all temperatures are in degrees Celsius.

EXAMPLE

Materials and Methods

Culture Lysates

*Neisseria gonorrhoeae,* culture F62, was obtained from the Center for Disease Control, Atlanta, Ga., and cultivated in GC broth, a medium containing, per liter of water, 15 g. protease peptone #3 (Difco Laboratories, Detroit, Mich.), 1 g. cornstarch, 4 g. dipotassium phosphate, 1 g. potassium dihydrogen phosphate, 5 g. sodium chloride, and 10 ml. IsoVitaleX Enrichment (IVX, Baltimore Biological Laboratories, Baltimore, Md.). Cells were cultured at ambient temperature, with shaking, for 24-48 hours. Cell lysates were prepared by centrifuging one liter of the resulting culture at 4,000×g for 30 minutes and suspending the pellet of cells thus obtained in 100 ml. of pH 9.0 0.1 M Tris buffer for one hour at 4°.

Cultures and lysates of other bacteria used and described herein were prepared as described above, except that lysis was aided by adding 1 mg/ml. lysozyme to the Tris buffer.

Antibody

Antibody to 1,2-propanediol dehydrogenase was prepared as described below.

The enzyme was purified by affinity chromatography, utilizing the techniques of Lee et al. for the preparation of the AMP-Sepharose affinity columns; see, e.g., C. Lee et al., *Arch. Biochem. Biophys.,* 163, 561 (1974) and C. Lee and N. O. Kaplan, *Arch. Biochem. Biophys.,* 168, 665 (1975). Briefly, adenosine 5'-monophosphate (5'-AMP) was brominated by addition to a solution of bromine in pH 4.5 0.25 M aqueous sodium acetate. The resulting 8-bromo-5'-AMP was isolated by column chromatography on a DEAE-cellulose column; the eluant was pH 7.8 0.5 M aqueous ammonium bicarbonate. The 8-bromo-5'-AMP was reacted with 1,6-diaminohexane in aqueous solution at pH 11.5 under reflux conditions to give 8-(6-aminohexylamino)-5'-AMP which was isolated by applying the crude product to an ion exchange column, and eluting the 8-(6-aminohexylamino)-5'-AMP with an acetic acid gradient (0-1 M, two liters per gram 5'-AMP derivative); fractions exhibiting an absorbance maximum at 280 nm were pooled and lyophilized. Covalent attachment of the 5'-AMP derivative to Sepharose 4B (Pharmacia Fine Chemicals, Inc., Piscataway, N.J.) was accomplished by means of cyanogen bromide activation; see, e.g, R. Axen et al., *Nature,* 214, 1302 (1967).

Complete Freund's adjuvant (CFA) was added to an equal volume of 0.01 M phosphate buffered saline (PBS), pH 7.4, which contained purified enzyme, and mechanically mixed for 25 minutes or until emulsification was complete. The resulting mixture was administered to a goat via multiple-site subcutaneous injections, with the first course involving a total of 0.2 mg. of enzyme. A booster dose of 0.6 mg. enzyme was necessary to raise the titer to an acceptable level.

The antibody content of the goat's serum was measured by the ability of serum dilutions to inhibit the enzyme-catalyzed oxidation of 1,2-propanediol and reduction of NAD. Accordingly, the enzyme-inhibition (E-I) titer of an antiserum was defined as the greatest serum dilution capable of a 50% inhibition of 5 units of enzyme activity. The E-I titer of the antiserum thus obtained was 1:128. The antiserum contained 65 μg/ml. of precipitate antibody protein that, in excess, completely inhibited enzymatic activity. Immunodiffusion analysis of antibody and enzyme showed one precipitin band which was enzymatically active.

Immobilized antiserum (immobilized antibody, IMA) was prepared according to Weetall and Filbert, using controlled-pore glass having a particle size of one micron and an average pore diameter 500 Å, in a ratio of one gram of glass per four ml. of antiserum; see W. B. Jakoby and M. Wilchek, Editors, "Methods in Enzymology," Volume 34B, Academic Press, Inc., New York, 1974, pp. 59–72. Briefly, the glass was cleaned in 5% nitric acid solution, washed, and treated with a ten percent solution of γ-aminopropyltriethoxysilane in distilled water at a pH of 3.45. The resulting silanized glass was reacted with p-nitrobenzoyl chloride in chloroform containing ten volume percent triethylamine as a hydrogen chloride scavenger. Reduction of the nitro group then was accomplished by treating the p-nitrobenzoylaminoalkyl derivatized glass with ten percent sodium dithionite in water. The resulting p-aminobenzoylaminoalkyl derivatized glass was diazotized with nitrous acid generated in situ from hydrochloric acid and sodium nitrite. The diazotized product was washed and added to antiserum at pH 8–9.

Enzyme Activity

The substrate solution for determining enzyme activity consisted of 0.1 g. NAD, 1.0 ml. 1,2-propanediol, and 30 ml. pH 9.0 0.1 M Tris buffer which is 0.25 M in ammonium chloride. One unit of enzyme activity was defined as that activity which was sufficient to cause an initial rate of reduction of 1.0 micromole of NAD per minute at 23°. $K_m$ values were determined graphically on the immobilized antibody-enzyme (IMA-E) complex. IMA (2 mg.), saturated with enzyme, was mixed with substrate solution containing varying concentrations of 1,2-propanediol or NAD in a final volume of 3.0 ml. The various sample tubes were capped and incubated for 30 minutes at 25° on a rocker platform. After centrifugation (5 minutes at 3,000×g) at 23° to pellet the IMA-E complex, the absorbance of the supernatant liquid at 340 nm. was measured and corrected against a blank containing each substrate solution without enzyme. Under these conditions, the generation of NADH was linear with time for 45 minutes.

The IMA-assisted assay for 1,2-propanediol dehydrogenase was performed as follows. Lysate (0.2 to 0.5 ml.) to be tested for enzymatic activity was added to a tube containing 200 μg. of IMA and the mixture was incubated for 45 minutes at 37°. The IMA-E complex was washed twice with 3 ml. of Tris buffer; substrate (0.2 to 2.0 ml) was added and the resulting mixture incubated at 37° for 90 minutes. The NADH generated was measured at 340 nm. on a spectrophotometer or on a Turner Model III Fluorometer (Turner Associates, Palo Alto, CA.) with a neutral density filter, or qualitatively estimated visually under ultraviolet illumination using an SL-25 mineral light (Ultraviolet Products, Inc., San Gabriel, CA.). A blank was composed of IMA mixed with buffer in place of lysate and treated similarly.

Stability Studies

Heat stability was determined by treating samples of IMA-E complexes for two minutes at various temperatures. The effects of antiserum and different chemical agents were determined by mixing IMA-E complexes with each agent for 30 minutes at 23° and then washing the complexes twice with Tris buffer. Age stability was determined by measuring the activities of IME-A complexes kept at various temperatures.

After each treatment, substrate solution was added and the resulting mixture was incubated at 37° for 30 minutes. Again, absorbance at 340 nm. was measured and compared with an untreated sample (control).

Results

IMA performed like antiserum; the degree of enzyme recovery was directly proportional to the amount of IMA added. Table 1 shows the results of three experiments in which the calculated amount of enzyme activity adsorbed is compared with the activity recovered. Clearly, the enzyme utilization efficiency is high; in two of the three experiments, it was possible to show that 100 percent of the enzyme activity initially present but not remaining in the supernatant was in fact adsorbed on IMA.

TABLE 1

Adsorption and Recovery of Enzyme Activity by IMA

| | | | Absorbance at 340 nm. | | |
| --- | --- | --- | --- | --- | --- |
| | | | Activity Adsorbed on IMA | | |
| Experiment | Activity Added | Activity in Supernatant | Calculated[a] | Measured | % Calculated Activity Recovered |
| 1 | 0.67 | 0.34 | 0.33 | 0.23 | 70 |
| 2 | 1.06 | 0.63 | 0.43 | 0.43 | 100 |
| 3 | 0.70 | 0.36 | 0.34 | 0.34 | 100 |

[a] This value represents the difference between the activity added and the activity recovered in the supernatant.

A typical preparation of an IMA-E complex contained 10–20 milliunits of enzyme per mg. of glass. Enzyme activity was pH dependent; in the pH range from 5 to 10, activity increased sharply above about pH 7, with maximum activity occurring at pH 10 which also is the optimum pH for the free enzyme. However, since the antibody-enzyme (IMA-E) complexes dissociated at such optimum pH, subsequent studies were carried out at pH 9.0 where 75 percent of maximum activity was observed.

The Km value for a typical preparation of an IMA-E complex did not differ significantly from Km values, similarly obtained, for free or uncomplexed enzyme.

The IMA-E complex is stable for at least two minutes at temperatures up to about 50°; about 65 percent of activity was lost after treatment at 70° for two minutes, and all activity was lost at 95°.

Enzymatic activity of the IMA-E complex also can be affected by various chemical agents. For example, after 30 minutes, enzymatic activity was lost at extremes of pH (0.1 N hydrochloric acid and 0.1 N aqueous sodium hydroxide) and partially lost (42 percent to 74 percent loss) in the presence of such agents as 95 percent ethanol, 6 M guanidine hydrochloride, 2 percent p-chloromercuribenzoic acid, 10 percent sodium dodecyl sulfate, and 3 percent sodium hypochlorite. The complex was stable in the presence of 1 percent 2-mercaptoethanol and 10 mg. protease (Type III, Sigma Chemical Co., St. Louis, Mo. The complex also was stable in the presence of normal goat serum. Thus, only reasonable care need be exercised in assuring that interfering substances are not present when carrying out the methods of the present invention, since such interfering substances normally will not be present.

The sensitivity of the assay described and claimed herein is in part dependent upon the detection method used. Such assay sensitivity was demonstrated by conducting the IMA-assisted assay for 1,2-propanediol dehydrogenase as already described, using a constant amount of IMA and decreasing, known amounts of enzyme. The results are shown in Table 2.

TABLE 2

Assay Sensitivity with Detection by Spectrophotometer, Fluorometer, and Visible Fluorescence Under Ultraviolet Illumination

| Milliunits Enzyme Offered to Constant Amount of IMA | IMA-E Enzyme Activity | | |
|---|---|---|---|
| | Spectrophotometer O.D. at 340 nm | Fluorometer RFU[a] | Visible Rating[b] |
| 50 | 1.7 | >100 | 3 |
| 5 | 0.45 | >100 | 3 |
| 0.5 | <0.02 | >100 | 3 |
| 0.1 | <0.02 | 80 | 2 |
| 0.05 | <0.02 | 25 | 1 |
| 0.02 | <0.02 | 14 | 1 |
| 0.01 | <0.02 | 8 | 0 |

[a] Relative fluorometer units, neutral density filter, sensitivity ×3.
[b] Scale of 0-3, where 0 = no fluorescence, 1 = slight fluorescence, 2 = moderate fluorescence, and 3 = strong fluorescence.

The detection of NADH by visual observation under ultraviolet illumination clearly is almost as sensitive as the fluorometer which is known to be of the order of 25 times more sensitive than the spectrophotometer. Thus, the spectrophotometer did not distinguish amounts of enzyme offered below about 5 milliunits, whereas the fluorometer and visual observation technique were able to distinguish amounts of enzyme offered as low as about 0.02 milliunits. Thus, detection methods based on fluorescence clearly are more sensitive than the spectrophotometric detection procedure and, hence, are preferred.

To evaluate the specificity of the disclosed assay, lysates from organisms having enzymes capable of oxidizing 1,2-propanediol and reducing NAD (e.g., glycerol dehydrogenase) were tested in such assay. The rsults are presented in Table 3, which compares the enzymatic activity of the lysates with the activity adsorbed by a constant amount of the IMA.

TABLE 3

Specificity of IMA Adsorption

| Lysate Source | Relative Fluorometer Units | |
|---|---|---|
| | In Lysate | Adsorbed |
| Neisseria gonorrhoeae | 46.5 | 39 |
| Staphylococcus epidermidis | 38 | 2.8 |
| Enterobacter cloacae | 33 | 2.1 |
| Escherichia coli | 48 | 2.8 |

It is to be understood that the foregoing detailed description is given merely by way of illustration and that many variations may be made therein without departing from the spirit of the invention.

For example, the method described herein has the sensitivity, specificity, and simplicity which permit adapting the method to a presumptive test for the presence or absence of *N. gonorrhoeae* infection which is carried out in the presence of the patient. In such a case, the presence of NADH is detected by visual observation under ultraviolet illumination. Even greater simplicity can be achieved by immobilizing the antibody on glass fibers, filters, rods or sticks, cellulose acetate strips, or any other supports which will adsorb antibody and have an appropriate geometry. Such supports often can be saturated with buffer and/or substrate solution, thereby eliminating the need for separate reagents. After lysis and a suitable incubation period, all that is necessary is to observe the support under ultraviolet illumination for the presence or absence of NADH-induced fluorescence.

It also should be apparent that the presence of NADH can be detected by other means. For example, the substrate solution can include a dye or dye formulation which is reducible by NADH, thereby permitting visual observation of color formation or a color change or the use of colorimetric procedures using a spectrophotometer. Examples of such dyes or dye formulations include a mixture of nitroblue tetrazolium and phenazine methosulfate and a mixture of iodonitrotetrazolium, diaphorase, and semicarbazide hydrochloride. Similar dye formulations are commercially available and are routinely sold as kits for the detection of lactate dehydrogenase.

What is claimed is:

1. A method for detecting the presence of Neisseria bacteria in a fluid sample which comprises bringing immobilized antibody specific for the enzyme 1,2-propanediol dehydrogenase which is released from such bacteria upon lysis thereof, into contact with a lysed sample, isolating the immobilized antibody or resulting immobilized antibody-enzyme complex having substantial 1,2 propanediol dehydrogenase activity or mixture thereof, and then testing the isolated material for enzymatic activity.

2. The method of claim 1 in which the antibody is immobilized on a particulate inorganic support.

3. The method of claim 2 in which the support is siliceous.

4. The method of claim 3 in which the support is controlled-pore glass.

5. The method of claim 1 in which the fluid sample is derived from a human body fluid or exudate.

6. The method of claim 1 in which the Neisseria bacteria are of the species *N. gonorrhoeae*.

7. A method for detecting the presence of Neisseria bacteria in a fluid sample which comprises the steps of:
   A. preparing a lysate of such sample;
   B. combining the lysate with an immobilized antibody specific for the enzyme 1,2-propanediol dehydrogenase;
   C. incubating the mixture resulting from step B;
   D. separating from the incubated mixture of step C the immobilized antibody or resulting immobilized antibody-enzyme complex having substantial 1,2 propanediol dehydrogenase activity or mixture thereof; and
   E. assaying the material obtained from step D for 1,2-propanediol dehydrogenase activity.

8. The method of claim 7 in which the antibody is immobilized on a particulate inorganic support.

9. The method of claim 8 in which the support is siliceous.

10. The method of claim 7 in which the support is controlled-pore glass.

11. The method of claim 7 in which the fluid sample is derived from a human body fluid or exudate.

12. A reagent system comprising an antibody which is immobilized on a support and is specific for propanediol dehydrogenase, wherein said antibody is capable of complexing with said enzyme resulting in a complex having sustantial 1,2 propanediol dehydrogenase activity, and substrate for said enzyme saturated on said support.

13. The complex reagent system of claim 12 in which the antibody is immobilized on a particulate inorganic support.

14. The reagent system of claim 13 in which the support is siliceous.

15. The reagent system of claim 14 in which the support is controlled-pore glass.

16. The reagent system of claim 12 in which the antibody is immobilized on a non-particulate support.

17. The reagent system of claim 16 in which the support is glass fibers.

18. The reagent system of claim 16 in which the support is cellulose acetate.

* * * * *

UNITED STATES PATENT AND TRADEMARK OFFICE
CERTIFICATE OF CORRECTION

PATENT NO. : 4,254,218
DATED : March 3, 1981
INVENTOR(S) : Hugh McDonald, Gerald Odstrchel, Milton M. Takeguchi It is certified that error appears in the above-identified patent and that said Letters Patent are hereby corrected as shown below:

Column 1, line 24, change "4,188,381" to -- 4,188,371 --.

Column 9, line 37, change "rsults" to -- results --.

Signed and Sealed this

Thirtieth Day of June 1981

[SEAL]

Attest:

RENE D. TEGTMEYER

Attesting Officer

Acting Commissioner of Patents and Trademarks